United States Patent [19]

Farah

[11] Patent Number: 4,912,049

[45] Date of Patent: Mar. 27, 1990

[54] PROCESS FOR THE PREPARATION OF CELLULOSE FILM, CELLULOSE FILM PRODUCED THEREBY, ARTIFICIAL SKIN GRAFT AND ITS USE

[75] Inventor: Luiz F. X. Farah, Curitiba, Brazil

[73] Assignee: Bio Fill Produtos Biotechnologicos S.A., Parana, Brazil

[21] Appl. No.: 878,880

[22] PCT Filed: Sep. 30, 1985

[86] PCT No.: PCT/BR85/00008

§ 371 Date: Jun. 10, 1986

§ 102(e) Date: Jun. 10, 1986

[87] PCT Pub. No.: WO86/02095

PCT Pub. Date: Apr. 10, 1986

[30] Foreign Application Priority Data

Oct. 1, 1984 [BR] Brazil ............................. 8404937[U]

[51] Int. Cl.$^4$ .................. C12R 1/02; C12P 19/04; C08B 00/00; A61K 47/00
[52] U.S. Cl. .................................. 435/823; 435/101; 536/56; 514/781
[58] Field of Search .................. 536/56; 435/101, 823; 514/781

[56] References Cited

PUBLICATIONS

"Utilization of Bio Fill in Burn Care" by Oliveira et al., of the Hospital Da Lagoa, Rio de Janeiro.
"Bio Fill, Use and Clinical Evaluation of a Cellulose Film on Cutaneous Lesions" by Peixoto and dos Santos, *Revista Brasileira de Circurgia* (1988), 78, No. 2
"A New Biological Dressing in Burn Care" presented by Cabral et al., The VIIth Ibero-Latin American Plastic Surgery Congress.
"Biological Dressing in the Care of the Severly Burnt" by Cabral et al., Revista *Brasileira de Circurgia* (1987), 77, No. 6.

*Primary Examiner*—Ronald W. Griffin
*Assistant Examiner*—Pamela S. Webber
*Attorney, Agent, or Firm*—Beveridge, DeGrandi & Weilacher

[57] ABSTRACT

There is described a process for the preparation of cellulose film, comprising the steps of preparing a culture medium having as nutrients sources of nitrogen and of carbohydrate, seeding this medium with a culture of acetobacter, species Xylinium; incubating the culture at temperatures which permit bacterial activity for a time suitable to the final intended use of the film, and removing the formed film from the culture medium for dehydration in a distended state. The film thus prepared is suitable for use as an artificial skin graft, a separating membrane, or artificial leather.

10 Claims, No Drawings

PROCESS FOR THE PREPARATION OF CELLULOSE FILM, CELLULOSE FILM PRODUCED THEREBY, ARTIFICIAL SKIN GRAFT AND ITS USE

The present invention relates to artificial skin grafts, and more particularly provides a process for the preparation of artificial skin.

Skin lesions have always been a grave problem to be confronted by medicine, particularly those lesions caused by burns. In these cases, the patient suffers extensive hydro-electrolitic losses, these losses being greater as the extent of the burned area increases. There is a critical period of approximately 36 hours in which substantial loss of blood fluids occurs in the burned region. After this period, this fluid loss is interrupted by the closure of the tissues, and the opposite effect is noted, i.e. a fluid retention which causes swelling. In cases where the area affected is great, the consequences can be fatal.

These extreme symptoms provoked by loss of skin through burns from heat radiation or chemical products also occur to a lesser extent in cases where skin loss is occasioned by abrasion or other mechanical causes. The conventional treatment, which is long and painful, consists in the continued application of medications, such as ointment, lubricated gauze, and bandages for retaining the gauze in place. The affected region is kept covered, and the patient receives large doses of antibiotics to prevent infection. For many years the above described problems have been tackled by applying skin substitutes to the affected area. The incessant search for solutions to these problems is illustrated by a vast bibliography of more than 120 studies published in the last ten years throughout the world, concentrating on attempt to find a skin substitute having the same properties and characteristics as human skin.

To date, the following human skin substitutes exist:
1. Autogenous grafting, in which skin is taken from another location on the patients body;
2. Heterogeneous grafting, which may be of two types:
   firstly, either human skin from donors or cadavers, or amniotic membrane from donors may be used;
   secondly, skin from pigs or bovine embryos, or artificial skins such as silicon, collagen, mixtures of collagen and silicon, or polytetrafluoroethylenepolyurethane.

Briefly, these items may be described in the following manner:

Autogenous grafting

This involves a surgical operation, extracting an area of the patients own skin from an elected donor region, to be immediately applied over the lesioned area. Since this causes a trauma equivalent to a second degree burn, this is only justifiable in patients who have third degree burns.

Heterogenous grafting

The first method uses human skin from donors, this method being extremely rarely used since as well as requiring donors to submit themselves to extensive traumas, the benefits of this type of grafting are transitory as the graft only lasts for a maximum of two weeks.

Human skin from cadavres

This type of grafting is almost never used, due to the inherent difficulties in obtaining cadavres at the appropriate time, together with their entire medical histories. There also exist ethical and legal difficulties, as well as objections from the family of the deceased.

Amniotic membrane

This requires a careful choice of donor, and the total absence of risk of contamination. The membrane must be prepared by a specialized team in a medical center, and must be done within twelve hours. As to its durability, like artificial skin substitutes it does not last more than a week.

Pigskin

Among the various animal skins exhaustively texted for use as human skin substitutes, pigskin presented the best results due to its anatomic characteristics similar to those of man. However, the necessary precautions and the preparation methods give this skin anatomic characteristics similar to man. However, the necessary care in the choice of animal and the preparation of a piece of skin make this option extremely laborious and complex.

The piglet of less than 5 months old, must be absolutely healthy and must have a skin free of any injury. The piglet is electrocuted and then decapitated so that all the blood is lost. A specialized team, working in a sterilizable atmosphere similar to a medical center removes all the skin of the piglet in a first stage, and thereafter prepares it into sheets using electrical equipment. The sheets must be stored under refrigeration (maximum temperature 4° C.) in physiological serum with antibiotics. This "skin" once applied to the patient has a limited durability of two weeks.

Artificial skins

Various studies have been carried out over the years in attempts to use synthetic products as skin substitutes for lesions where skin loss has occurred. Two lines of research are worthy of note, the first being the search for a substitute prepared totally from synthetic substances such as silicon, polyurethane, and others, the second attempting to associate a synthetic film of organic material prepared from derivatives of animal blood such as for example collagen.

The first, a completely synthetic skin, has not yet passed through the investigative stage and no product has been placed on the market. The second refers to an artificial skin, prepared from two integral layers. The layer which enters in contact with the lesion is formed from dried organic material, preferably derived from animal bood, and the other is silicon, polyurethane, or the like and functions as a support, this layer being exposed. The organic part is absorbed by the organism, and the support is then rejected. A product is being marketed, and its characteristics are described in Brazilian patent No. PI 7800285, patentee Battelle Memorial Institute.

The present invention resolves the problems described above in a suprising and totally unexpected way, by providing a cellulosic film of varying thickness. The film is translucent, and has selective permeability. The film is pleasant to the touch, and very similar to human skin, the film being semi-permeable, elastic, and having great adhesive power when in contact with the exudate which covers the lesion area. The film has none of the previously mentioned disadvantages, and in addition provides the following advantages in relation to the prior art:

The film is of low cost, easy preparation, and may be sterilized without deterioration.

The esthetic aspect is pleasant, which favours the patient psychologically.

The film is easily applied, the use of dressings being unnecessary.

The film is adapted to any body location, since it easily adheres to lesioned regions by their exudate, and has sufficient elasticity to permit movement.

The film is easily stored, since it is not perishable and does not need refrigeration.

Application of the film immediately relieves pain since it protects the nerve endings.

The strong adhesion of the film to the wound reduces the proliferation of germs, and leaves the wound hermetically sealed.

Hydro-electrolytic losses are reduced. A shortening of the scar forming time in second degree burns, and the tissue granulation in third degree burns.

No formation of retractile scarring occurs.

Since there is no need to change dressings, the risk of contamination is deminished.

There is no allergic reaction.

The film permits visual inspection of the development of the treatment, by its translucence. This is in contrast with the artificial skins presently existent.

The film must be applied delicately over the injured region, so as to prevent the inclusion of air bubbles or bood secretions between the wound and the film. Once in position on the exudate, and covering the lesion completely, the film gradually and slowly absorbs the exudate. Due to this slowness, the film provides conditions for coagulation of the exudate within the flm, thus forming a bridge between the film and the lesioned area. Also due to the slow absorption, coagulation occurs before the exudate has penetrated the membrane, coagulation occurring in two areas;

(a) the microscopic spaces existing between the films fibers;

(b) the surface of the injury.

From this, there results a perfect adhesion preventing hydro-electrolytic losses and substantially reducing the risk of infection. Additionally, since the nerve endings are isolated, the pain of the injury is immediately reduced.

The film, therefore, makes it possible for the patient to reconstitute the epithelial tissues, since the lesioned area is isolated and contamination is avoided. Under these conditions, there is no necessity to change dressings, since the adhesion of the film to the lesion will only cease gradually, as the tissue regenerates. The film is formed totally from cellulose, an inert substance, and does not have any medicinal action on the lesioned zone. After having provided the organism with conditions to regenerate the lesioned tissues, the film ceases to adhere to the patient, and leaves no residue whatsoever on the regenerated area. The film becomes unstuck, with exactly the same characteristics it had at the moment of its application, and may be regarded simply as a prosthesis or temporary implant.

Since the cellulose film is strong and inert, it permits of practically all types of sterilization. It may be stored at any temperature, and does not require special conditions. It is of unlimited durability. The film has determined permeability to liquids and air, a characteristic molecular weight and structure, a predictable thickness when dehydrated, in addition to other specific physical characteristics.

The following physical and spectroscopic studies were made with the objective of better defining the material of the present invention.

To this end, a sample of the film was partially whitened using a 30% sodium hypochloride solution, the whitened part being subsequently dyed, leaving a remainder in its original, non-whitened condition. The following results were obtained:

| Tests | Film Whitened | Film Non-Whitened |
|---|---|---|
| 1. Permeability to air, Bendtsen, mL/min (150 WG) | 11 | 8 |
| 2. Resistance to air, Gurley, s/100 mL NBR 7152/82 (ABNT MB-1271/79) | more than 1800 seconds | more than 1800 seconds |
| 3. Tensile strength, kg/cm² NBR 7462/82 (ABNT-MB 57/68) | — | 7,92 |
| 4. Elongation, % NBR 7462/82 (ABNT-MB 57/68) | — | 74 |

Note:
For the physical tests, the film was brought to a moisture content of 25 ± 5% and the proof bodies were packed and tested at a relative humidity of 65 ± 2% and a temperature of 20 ± 1° C.

Spectroscopic analysis revealed that both the whitened and non-whitened films were of cellulosic nature.

In the spectroscopic study, the following reference table was used, the table having been taken from "infrared spectra of cellulose and its derivatives" by Rostislav Georgievich Zhbankov, and published in 1966.

REFERENCE TABLE

| Group/bonding | Compound | Wave number cm$^{-1}$ |
|---|---|---|
| 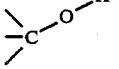 | cellulose and its derivatives | from 1400 to 1200 |
| 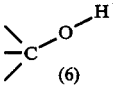 (6) | cellulose and its derivatives | from 1400 to 1300 |
| 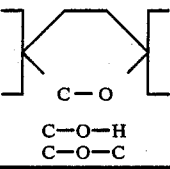<br>C—O<br>C—O—H<br>C—O—C | cellulose and its derivatives | from 1200 to 1100<br>from 1150 to 1000 |

The process for preparation of the film is a biosynthesis which takes place during the reproduction of bacteria of the order pseudomonadales, from the family of pseudononadaceas, of the genus acetobacter, species Xylinum. These bacteria, seeded in a culture medium, having carbohydrate nutrients associated with a nitrogen source, produce a cellulosic capsular zoögloea which surrounds the microorganisms.

This zoögloea has a cartilaginous appearance and a thickness which varies between 0.2 and 400 mm. After seeding the bacteria, a schizogenous vegetative reproduction process is initiated; the cell is divided in two equal parts and grows until a central ring is formed, where the bacterium divides. In the case of acetobacter, after cellular division the new bacteria is aggregated to its originating bacteria and immediately initiates its own reproductive process. Under ideal conditions, a further division occurs each 20 minutes.

The acetobacters are surrounded by a cellulosic capsule and after division they remain agglomerated, forming chains. This characteristic, allied to the speed of reproduction, propiciates the formation of a cellulosic film by the linking of the bacterial chains with their respective capsules.

The thickness of the film is variable and depends on various factors, such as the dosage of nutrients, temperature, time, saturation point of the colony, and the type of culture medium.

The zoögloea of the acetobacters is a fabric formed by the interweaving of the bacterial chains surrounded by their cellulosic capsules. Proceeding with the dehydration of the zoögloea, there are obtained sheets of pure cellulose which, by their characteristics, permit their use as raw material for various industrial purposes, among these dermatological prostheses, suture medium, or leather substitutes.

After dehydration the microscopic spaces existing between the fibres of the membrane offer selective permeability characteristics.

The thickness of the film is a function of the following variables, interalia:

(a) the content of carbohydrates in the culture medium;
(b) the content of nitrogen in the culture medium;
(c) the temperature;
(d) the duration of the period of formation of the zoögloea.

Various examples will now be given to illustrate the invention, the examples being non-limitative.

EXAMPLE 1

A culture medium was prepared from an infusion of 20 g of Tea Sinensis in 10 liters of water. The infusion was filtered, and 1 kg of sugar was added to the filtrate, which was then mixed.

To the culture medium obtained, 10 ml of a culture of acetobacter, species Xylinum was added, and was incubated at 28° C. for a period of 36 hours, a thin film being formed of approximately 0.2 mm thickness.

The film is removed from the medium, and is optionally boiled depending on its intended use and is then dehydrated at ambient temperature on supports, in a distended state. The film thus obtained is then ready for use as artificial skin or leather. The culture medium separated from the skin is filtered, and is made up with the nutrient solution initially used to compensate for losses which occur during the biosynthesis process.

The temperature of incubation and the concentration of carbohydrates in the culture medium are not critical, and may vary between very low levels which still permit bacterial activity and high levels which still permit existence of the film without causing deformation thereof.

The temperature of dehydration is also not critical, and normal heat sources may be used.

EXAMPLE 2

The process of example 1 is followed, the culture being left to incubate during a period of 96 hours, whereupon a film of zoögloea of 3 mm thickness was obtained, the film being usable after dehydration as an artificial skin graft.

EXAMPLE 3

The process of example 1 was used, using as a source of nitrogen, maté.

A film identical to that of example 1 was obtained, with the same predehydration thickness, the incubation time being 72 hours.

EXAMPLE 4

A film prepared in accordance with the previous examples was taken and delicately applied on a lesioned region where loss of epithelial tissue had occurred, so that between the film and the injury no air bubbles or blood secretions were formed. Once the film was applied over the exudate, completely covering the lesion, the film absorbed the exudate but did not permit loss of exudate nor entry of air.

The film therefore forms a new skin over the tissue, mechanically eliminating pain symptoms by isolating the nerve ending. The lesion regenerates after a time, and the film spontaneously lifts from the region after its regeneration leaving visible a new epithelial tissue completely regenerated.

The cellulose film of the invention may also be used as a surgical suture, given the necessary preparation, and presents a high knot strength.

The film may also be used as a separating membrane, as artificial leather, for tennis racket strings, or any other of the uses to which cellulose is normally put.

I claim:

1. A liquid gas permeable cellulose film, produced according to the process comprising the steps of:
   preparing a culture medium having as nutrients a carbohydrate nutrient and a source of nitrogen;
   seeding in this medium a culture of Acetobacter, species xylinum;
   incubating the culture at temperatures which permit the activity of the bacteria during a time suitable for the intended use of the film; and
   withdrawing the formed film from the culture medium and dehydrating it while it is stretched.

2. A cellulose film according to claim 1 wherein the nitrogen source is Tea Sinensis, and the carbohydrate nutrient is sucrose.

3. A cellulose film according to claim 1 having a thickness of 0.2 to 3 mm prior to dehydration.

4. A cellulose film according to claim 2 having a thickness of 0.2 to 3 mm prior to dehydration.

5. An artificial skin graft comprising a dehydrated liquid and gas permeable cellulose film according to claim 1 which has been cut to size after the dehydration step, sterilized, and packaged.

6. An artificial skin graft comprising a dehydrated liquid and gas permeable cellulose film according to claim 2 which has been cut to size after the dehydration step, sterilized, and packaged.

7. An artificial skin graft comprising a dehydrated liquid and gas permeable cellulose film according to claim 3 which has been cut to size after the dehydration step, sterilized, and packaged.

8. An artificial skin graft comprising a liquid and gas permeable cellulose film according to claim 1.

9. An artificial skin graft comprising a liquid and gas permeable cellulose film according to claim 2.

10. An artificial skin graft comprising a liquid and gas permeable cellulose film according to claim 3.

* * * * *